United States Patent [19]

Yun et al.

[11] Patent Number: 4,956,067

[45] Date of Patent: Sep. 11, 1990

[54] MULTI-ROTATING DISK ELECTRODE AND SOLID POLYMER ELECTROLYTE ELECTRODE TYPE ELECTROLYTIC BATH

[75] Inventors: Kyung S. Yun; Byung W. Cho, both of Seoul, Rep. of Korea

[73] Assignee: Korea Institute of Science and Technology, Seoul, Rep. of Korea

[21] Appl. No.: 460,986

[22] Filed: Jan. 4, 1990

[30] Foreign Application Priority Data

Sep. 6, 1989 [KR] Rep. of Korea .......... 12904/1989[U]

[51] Int. Cl.$^5$ ................................................ C25B 9/00
[52] U.S. Cl. ..................................................... 204/212
[58] Field of Search ......................................... 204/212

[56] References Cited

U.S. PATENT DOCUMENTS 4,125,439 11/1978 Fleischmann ....................... 204/212

OTHER PUBLICATIONS

Colin Oloman, AICHE Symposium Series 229, vol. 70, 68 (1983), Hiragame Koryo and Nishiguni Yoozo, Chemical Industry, 36 (10), 721 (1985).

*Primary Examiner*—T. M. Tufariello
*Attorney, Agent, or Firm*—Birch, Stewart, Kolasch & Birch

[57] ABSTRACT

Multi-rotating disk electrode and solid polymer electrolyte electrode type electrolytic bath in which surface area augment of electrode and agitation of solution are improved by multi-RDE while migration of reaction material and produced material toward other chamber is prevented by utilizing SPE electrode, whereby exhibiting high reaction yield under low electrolytic voltage. The invention is constituted such that multi-RDE electrode formed by stacking alternately circular shaped large RDEs and small RDEs, and SPE electrode combined with electrically conductive material such as metal in single layer or multiple layers on SPE surface, are simultaneously provided. According to the invention, higher reaction yield can be obtained than any other electrolytic synthesizing method as well as electrolytic bath.

8 Claims, 2 Drawing Sheets

MULTI-ROTATING DISK ELECTRODE AND SOLID POLYMER ELECTROLYTE ELECTRODE TYPE ELECTROLYTIC BATH

BACKGROUND OF THE INVENTION

The present invention relates to an electrolytic bath that the working electrode is composed of multi-rotating disk electrode (hereinafter refered to as multi-RDE) and solid polymer electrolyte (SPE) electrode, more particularly to a novel multi-rotating disk electrode and solid polymer electrolyte electrode type electrolytic bath in which the surface area of electrode is increased and the agitation effect in solution is improved by multi-RDE, while the migration of reactants and reaction product toward other chambers is prevented by utilizing SPE electrode, whereby high reaction yield is obtained under lower electrolytic voltage.

Various kinds of electrolytic bath utilized for the industry have been known, and the typical electrolytic baths for the industry include, for example, capillary gap electrolytic bath, Swiss roll electrolytic bath, electric charge layer electrolytic bath, fluid layer electrolytic bath, slurry electrolytic bath, gas diffusion electrolytic bath, SPE electrolytic bath and rotary electrode electrolytic bath [refer to Colin Oloman, AICHE Symposium Series 229, Vol, 79, 68 (1983) and Hiragame Koryo and Nishiguni yoozo, Chemical Industry, 36(10), 721(1985)].

The respective features of the above mentioned baths are described briefly in the followings.

Firstly, tank type electrolytic bath is an electrolytic bath of the most fundamental form in which a plurality of positive electrodes and negative electrodes are mounted on the interior of electrolytic bath whereby current distribution is uniform, while it has advantage that the workability is better and repairing is easier, but there has been some problems that it is unsuitable for electrolytic organic synthesis since the production quantity can not be increased and mixing of solution is insufficient.

Next, filter press type electrolytic bath is composed of a plurality of positive electrodes and negative electrodes neighbouring each other and thereby having an advantage that electrode area can be increased and distance between electrodes can be reduced, and it is used much for industrial purpose, because the production quantity can be increased, however it has disadvantages that their assembling and repairing works are complicated, and when the solid substance is produced within electrolytic solution, the said solid substance blocks the inlet of electrolytic solution.

Capillary gap electrolytic bath is of the type that the distance between electrodes is minimized so that the electrolytic solution may be flowed in high speed, which has property suitable for non-aqueous solution electrolyte of single phase, but having problems that it is not suitable for multiple electrolyte and requiring more pump driving power.

Swiss roll electrolytic bath is of the type that the isolating film having a good flexibility and electrode as well as spacer are stacked to assembly in the sandwitch manner, which exhibits disadvantage that the current density cannot be increased much more.

Electric charging layer electrolytic bath is a matter that the particle electrode is charged and thereby the surface area of electrode is extremely increased, but has a problem in contacting between the electrode and the power supply source.

Fluid layer electrolytic bath is a matter that the particle electrode is mounted in fluidized state, it is unsuitable for multiple electrolyte and has also a problem in contacting between the electrode and the power supply source.

SPE electrolytic bath is of the type that electrodes are formed on one side or both sides of ion exchange membrane, which includes an advantage that the supporting electrolyte is not necessary and the electrolysis is possible even in organic solvent of non-polarity, but has problems that the manufacturing of electrode is not easy and the material migration is not suitable for the reaction of the rate determining step.

RDE is of the type that the electrode rotates, which is used much for laboratory purpose, and since the material migration speed can be considerably increased and, at the same time the material migration phenomenon is well arranged theoretically, the RDE is used much for examining the reaction mechanism of the electro chemical reaction, however, since only one side of electrode is used, the surface area of the electrode is relatively small, and in case of being used for the industrial purpose, the high speed rotation is impossible so that the agitation in solution can not be carried out sufficiently, it is almost not used for the industrial electrolytic bath.

SUMMARY OF THE INVENTION

Therefore, it is an object of the present invention to provide an improved multi-rotating disk electrode and solid polymer electrolyte electrode type electrolytic bath in which of the surface area of electrode and agitating effect in solution are increased through multi-RDE formed by stacking a plurality of RDE, while SPE electrode is provided together with said multi-RDE and the migration of reactants and the reaction product toward the other chamber is prevented so that the reaction yield is increased.

Another object of the present invention is to provide a multi-rotating disk electrode and solid polymer electrolyte electrode type electrolytic bath in which electrolysis is possible by the good agitating effect in solution according to the using of multi-RDE as in organic electrolytic syntnesis in a state of without using solvent and surfactant required for dissolving and dispersing of reaction material, at the same time, exhibiting low electrolytic voltage based on the increased electrode surface area.

According to the multi-RDE in the electrolytic bath of the present invention, since the agitating effect in solution is good and the surface area of the electrade is considerably large, the improvement of productivity can be expected according to the increase of the material migration speed, particularly when the material migration speed is the rate determining step, it is characteristic of being capable of increasing the reaction yield by using multi-RDE.

On the other hand, in case of most organic electrolytic synthesis, since reactants and the reaction product produced from the working electrode are reacted at electrode couple to act as a decreasing factor for reaction yield, as a way for preventing such phenomenon, the positive electrode chamber and negative electrode chamber are isolated by ion exchange membrane and preventing the migration of reactants and the reaction product, however, the migration of reactants and the reaction product still exists even by providing such ion membrance, accordingly the reaction yield is decreased.

Therefore, the present invention has advantages that since the migration of reactants and reaction product toward other chamber through ion exchange membrance is prevented by providing multi-RDE together with SPE electrode descrease of the reaction yield is prevented, at the same time, the reduction of the electrolytic voltage in accordance with the electrode area increasing as much as SPE electrode can be expected.

Of course, although electrolytic synthesis is possible even by use of only SPE electrode without using multi-RDE in case of the electrochemical reaction that the material migration is the rate determining step, the reaction yield is reduced by only SPE electrode, and also when the current density is high, SPE electrode is released away and causing the loss of electrode. Thus, since it has some difficulties in executing electrochemical reaction by only SPE electrode, it is desirable to use simultaneously the multi-RDE and SPE electrode as in the present invention.

DETAILED DESCRIPTION OF THE INVENTION

Figure 1:
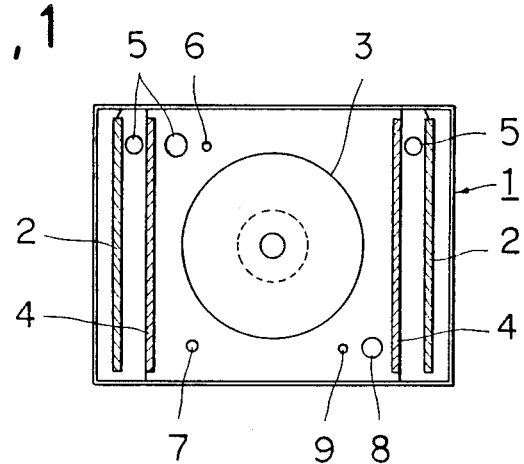
FIG. 1 is a plan view of an electrolytic bath of the present invention.
Figure 2:
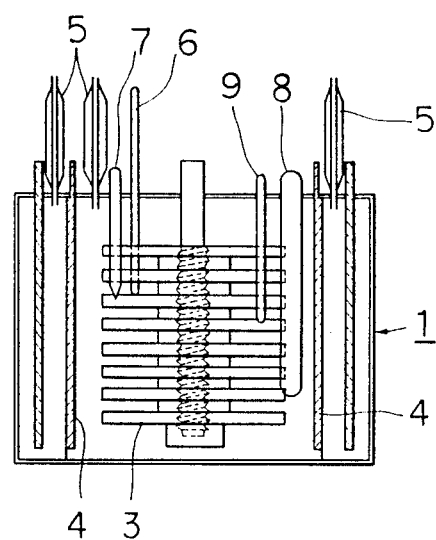
FIG. 2 is a longitudinal sectional view of the electrolytic bath of FIG. 1.

Referring to FIG. 1 and FIG. 2, electrode couples 2 are mounted at both sides of the interior of electrolytic bath 1, and multi-RDE 3 formed by stacking alternately with a plurality of large and small disk type RDE are formed at the center thereof, at the same time, SPE electrodes 4 are formed respectively between large electrodes 2 and multi-RDE.

In the drawings, reference numeral 5 is condenser, 6 is thermometer, 7 is reference electrode, 8 is heater, and 9 is thermometer.

Figure 3:
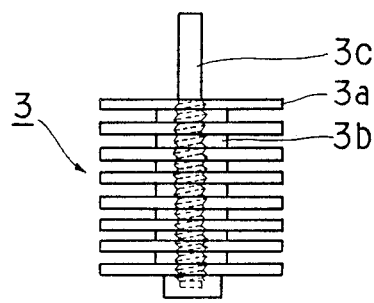
FIG. 3 is an enlarged view of a multi-RDE of the present invention.

Explaining multi-RDE 3 in more detail, as shown in FIG. 3, multi-RDE 3 is structured such that disk shaped large RDE 3a and small RDE 3b having circular holes at the center thereof are formed by stacking alternately on one single center shaft, and they are coupled with metal electricity collector 3c formed with male screw thread means on circumferential surface thereof as an extension of motor shaft through circular holes of said center portion.

As a material for the RDE, metal such as copper, iron, lead and carbon capable of being made in the form of plate are used, and it is also possible that sheet like RDE coated with precious metal on the surface thereof or amalgamated one/is used. And the size of RDE is changed according to the condition of the electrolytic reaction, however, substantially 10–200 cm in diameter and 1–30 mm in thickness for large RDE 3d are preferable and 2–20 cm in diameter and 114 5 cm in thickness for small RDE 3b are preferable.

Further, metal electricity collector 3c as a rotary shaft for rotation and electric power supply of multi-RDE 3 is in the range of 1–10 cm in diameter and male screw thread is formed on its circumference, which is coupled with the multi-RDE formed by stacking alternately a plurality of large RDE 3a and small RDE 3b. The height of multi-RDE is preferably 10–20 cm.

Figure 4:
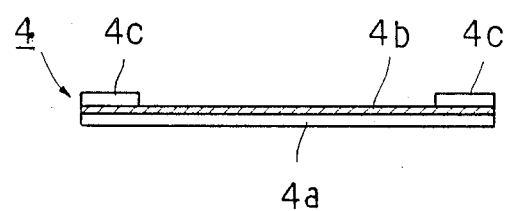
FIG. 4 is an enlarged view of a SPE electrode of the present invention.

Next, SPE electrode 4 is structured such that, as shown in FIG. 4, metal electrode 4b made of a material such as copper or bismuth is formed on one surface of ion exchange isolation membrane 4a, and metal electricity collector 4c made of a material such as copper or titanium is attached on both sides of the metal electrode 4b.

The SPE electrode is of the type combined with electronically conductive material such as metal in single or multiple layers on SPE surface, and various methods including chemical depositing method, physical depositing method and non-electrolytic plating method are known for the combining method of the electronically conductive material, however, non-electrolytic plating method is most economical and efficient relative to the others.

Particularly, the permeating method is more utilized than various non-electrolytic plating methods, in which permeating method is a method that a reducing agent in solution for example: aqueous hydrazine solution is put into one side of ion exchange membrane, and solution containing metal ion to be extracted is put into another side, and then the reducing agent passes through SPE to reduce the metal ion at opposite surface whereby extracting the metal on SPE surface.

At this moment, various kinds of solution including hypophosphate other than hydrazine can be used for reducing agent, and various kinds of metals such as platinum, nickel, copper, lead and bismuth are used.

On the other hand, the rotational speed of multi-RDE can be decreased as the diameter of disk electrode is large, the range of desirable rotational speed is 100–3000 rpm. And, since the current density exhibits the reaction rate, there is advantage that productivity is increased in response to the increasing of current density, while there is also disadvantage that electrolytic voltage is raised and reaction yield is rather dropped in accordance with that.

Therefore, for the proper current density of the electrolytic bath according to the present invention, it is sufficient when it is 20–300 mA/cm$^2$ in case of multi-RDE and about 1/5–1/100 of multi-RDE current density in case of SPE, however, optimum current density is varied depending upon the electrolytic reaction characteristic and reaction condition. And, the completion of the electrolytic reaction can be recognized by providing a reference electrode within the interior of the electrolytic bath and by measuring the potential of the working electrode (multi-RDE) with respect to the reference electrode. In case that electrolytic reaction is completed, the potential of the working electrode is rapidly increased and become to reach a predetermined potential. At this moment, generally the saturated calomel (SCE) is much used for the reference electrode.

Electrolytic synthesis by electrolyzing from nitrobenzene to para-aminophenol by using electrolytic bath according to the present invention as aforementioned are illustrated in the following examples.

EXAMPLE 1

Electrolytic sythesis was carried out by using 2.5M sulfuric acid-1M nitrobenzene as solution of the negative electrode chamber and using 2.5M sulfuric acid as solution of the positive electrode chamber, setting multi-RDE and SPE copper-bismuth electrode made of graphite for negative electrode at 90° C., and setting Pb-Ag for positive electrode. Multi-RDE used at this moment was 60 mm in diameter and 5 mm in thickness for large RDE, 15 mm in diameter and 10 mm in thickness for small RDE, of which entire height being 10 cm.

And, the current of multi-RDE was set to 20A and the current of SPE copper-bismuth electrode was set to 2A and the electrolytic reaction was finished at the time when potential of multi-RDE was suddenly increased. The solution after electrolytic reaction was analyzed to obtain the reaction yield of 8% for para-aminophenol and 14% for anilin and the electrolytic voltage was 5.0V.

EXAMPLE 2

At a state that condition of solution and positive electrode were maintained same as example 1, the electrolytic synthesis was carried out at 22A of currenty by using only multi-RDE as negative electrode.

Electrolysis was finished at the time when potential of multi-RDE was suddenly increased. As a result after electrolyzing, the solution was anaiyzed to obtain the reaction yield of 80% for para-aminophenol, 18% for anilin and 2% for azoxybenzene, and the electrolytic voltage was 5.5V.

EXAMPLE 3

At a state that condition of solution and positive electrode were maintained same as example 1, electrolytic synthesis was carried out while stirring the solution at 22A of current by using only SPE copper-bismuth electrode for negative electrode.

Electrolysis was finished at the time when the potential of SPE electrode was suddenly increased, and the reaction yield after electrolyzing, obtained 70% for para-aminophenol and 30% for anilin, and the electrolytic voltage was 5.2V.

As can be seen from the aforementioned examples, it is appreciated that high yield is exhibited in case of using two electrodes simultaneously relative to that using multi-RDE and SPE electrode separately, at the same time, exhibiting low electrolytic voltage. Particularly, in electrolyzing and synthesizing the para-aminophenol from nitrobenzene by using electrolytic bath of the present invention, electrolyzing and synthesizing is carried out at a state without using the solvent required to dissolution or dispersion of nitrobenzene or else surfactant (U.S. Pat. No. 3,338,806 and No. 4,584,070), exhibiting reaction yield promoted about 10–20% relative to known electrolytic synthesizing method.

What is claimed is:

1. A multi-rotating disk electrode and solid polymer electrolyte electrode type electrolytic bath comprising:
   a multi-rotating disk electrode (RDE) which is formed by stacking alternately large and small rotating disk electrodes; and
   a solid polymer electrolyte (SPE) electrode in which conductive material such as metal is coupled in a single layer or multilayers on a solid polymer electrolyte, both of said multi-RDE and SPE electrode being provided simultaneously as a working electrode.

2. The multi-rotating disk electrode and solid polymer electrolyte electrode type electrolytic bath according to claim 1, wherein said multi-RDE is made of metal such as copper, iron, and lead capable of being manufactured into plate form, graphite and the materials coated with precious metal or amalgamated on the surfaces thereof.

3. The Multi-rotating disk electrode and solid polymer electrolyte electrode type electrolytic bath according to claim 1, wherein said large rotating disk electrode has the size of 10–200 cm in diameter and 1–30 mm in thickness, and said small rotating disk electrode is 2–20 cm in diameter and 1–5 cm in thickness.

4. The Multi-rotating disk electrode and solid polymer electrolyte electrode type electrolytic bath according to claim 1, wherein said multi-RDE is coupled with metal electricity collector of 1–10 cm in diameter by screw coupling through a hole formed at the center of said multi-RDE.

5. The multi-rotating disk electrode and solid polymer electrolyte electrode type electrolytic bath according to claim 1, wherein the height of said multi-RDE is 10–200 cm.

6. The multi-rotating disk electrode and solid polymer electrolyte electrode type electrolytic bath according to claim 1, wherein the current density of said multi-RDE is 20–300 mA/cm$^2$, and the current density of said SPE electrode is 1/5–1/100 relative to the current density of said multi-RDE.

7. The multi-rotating disk electrode and solid polymer electrolyte electrode type electrolytic bath according to claim 1, wherein the rotational speed of said multi-RDE is 100–300 rpm.

8. The multi-rotating disk electrode and solid polymer electrolyte electrode type electrolytic bath according to claim 1, wherein the completion of electrolysis is measured by potential raising of the multi-RDE against reference electrode.

* * * * *